(12) United States Patent
Morris

(10) Patent No.: US 12,329,933 B2
(45) Date of Patent: Jun. 17, 2025

(54) SYSTEM AND METHOD FOR ADMINISTERING RADIOACTIVE AGENTS TO A SUBJECT

(71) Applicant: Advanced Molecular Imaging and Therapy, LLC, Glen Burnie, MD (US)

(72) Inventor: Michael Morris, Glen Burnie, MD (US)

(73) Assignee: Advanced Molecular Imaging and Therapy, LLC, Glen Burnie, MD (US)

( * ) Notice: Subject to any disclaimer, the term of this patent is extended or adjusted under 35 U.S.C. 154(b) by 0 days.

(21) Appl. No.: 18/897,472

(22) Filed: Sep. 26, 2024

(65) Prior Publication Data

US 2025/0009969 A1 Jan. 9, 2025

Related U.S. Application Data

(63) Continuation of application No. 17/524,648, filed on Nov. 11, 2021.

(60) Provisional application No. 63/112,306, filed on Nov. 11, 2020.

(51) Int. Cl.
| | |
|---|---|
| *A61M 5/14* | (2006.01) |
| *A61M 5/142* | (2006.01) |
| *A61M 5/178* | (2006.01) |
| *G21F 5/00* | (2006.01) |
| *G21F 5/018* | (2006.01) |

(52) U.S. Cl.
CPC .......... *A61M 5/1785* (2013.01); *A61M 5/142* (2013.01); *G21F 5/018* (2013.01)

(58) Field of Classification Search
CPC ...... A61M 5/1785; A61M 5/142; G21F 5/018
See application file for complete search history.

(56) References Cited

U.S. PATENT DOCUMENTS

| | | | |
|---|---|---|---|
| 4,846,235 A | 7/1989 | Handke | |
| 6,576,918 B1 | 6/2003 | Fu | |
| 2003/0226983 A1 | 12/2003 | Zens | |
| 2022/0176040 A1* | 6/2022 | Morris | A61M 5/14546 |

OTHER PUBLICATIONS

Office Action issued in co-pending U.S. Appl. No. 17/524,648 on Feb. 13, 2025.

* cited by examiner

*Primary Examiner* — Nicole M Ippolito
(74) *Attorney, Agent, or Firm* — Whiteford, Taylor & Preston, LLP; Peter J. Davis

(57) ABSTRACT

An apparatus for shielding medical personnel from radioactive materials being administered to a patient in need thereof, including a radioactive syringe shield and a radioactive fluid pump shield. The radioactive syringe shield includes a syringe main body, and syringe shields proximal and distal ends each configured to attach to opposite ends of the syringe shield main body in a threaded male/female connection. Together, the syringe shield main body, and proximal and distal ends are configured to contain therewithin a medical syringe containing radioactive medical fluid. The radioactive fluid pump shield is a shielded box configured to contain the fluid pump and has top and front portions pivotally attached to adjacent portions to allow selective access to the fluid pump.

5 Claims, 6 Drawing Sheets

ND METHOD FOR
SYSTEM AND METHOD FOR ADMINISTERING RADIOACTIVE AGENTS TO A SUBJECT

BACKGROUND OF THE INVENTION

Field of the Invention

This invention relates generally to systems and methods for administering radioactive agents to a patient, and more particularly to systems and methods for transporting and administering a dosage of a radioactive agent, such as Zr-89 PET agents, for diagnostic imaging purposes, to a patient while minimizing exposure of the radioactive agent to medical personnel.

Description of the Background

Various radioactive agents are used in the medical field for a wide variety of purposes. For instance, positron emission tomography ("PET") imaging using radiolabeled monoclonal antibodies has been employed for imaging of tumors inside of a patient's body. This process may be similarly employed for therapeutic purposes.

To carry out such procedures, the radioactive agents must be injected into a patient and later detected by an imaging device, such as a PET scanner. Unfortunately, medical personnel preparing and transporting the dosage, along with those actually administering the dosage to the patient (and the patient themselves), may be exposed to radiation emitted from the dosage. Long term and repeated exposure to such radiation may be harmful to persons that are in the vicinity of the dosage.

In order to protect against such radiation exposure risks, the syringe containing the dosage is often transported in a lead "pig" that serves to at least partially shield those handling and transporting the dose to the patient. However, traditional lead pigs provide only limited shielding, such that medical personnel who are repeatedly exposed to radiation from such dosages remain at risk despite the use of a lead pig. Even further, the syringe must typically be removed from the pig so that the dosage may be administered to the patient. As the injection of various radioactive image agents may require that the injection take place over an extended timespan (e.g., 5 minutes or longer), the personnel administering the dosage and the patient themselves remain exposed to radiation from the dosage during the actual injection

SUMMARY OF THE INVENTION

The present invention provides systems and methods capable of reducing the risk of exposure to radiation to both medical personnel and patients when administering a radioactive agent, such as for purposes of imaging using a PET scanner.

Accordingly, there is provided according to one embodiment of the invention a syringe radiation shield comprising: a first rod having a first proximal end and a second distal end and a first rod central bore extending between and through said first and second ends, said first rod central bore dimensioned to receive a fluid containing portion of a medical syringe; a second rod having a third end and a fourth end, and a second rod central bore extending partially but not entirely from said third end toward said fourth end, wherein said third end is configured to attach to said second end of said first rod in a threaded male-female connection, said second rod central bore dimensioned to receive a fluid lock at a forward end of said medical syringe; and a third rod having a fifth end and a sixth end, and a third rod central bore extending partially but not entirely from said fifth end toward said sixth end, wherein said fifth end is configured to attach to said first end of said first rod in a threaded male-female connection, said third rod central bore dimensioned to receive a plunger portion of said medical syringe; wherein walls of said first, second, and third rods are made of a material and thickness sufficient to shield medical personal from radiation from radioactive materials contained in said syringe.

There is also provided according to another embodiment of the invention a fluid pump enclosure comprising: a rectangular box comprising front and back panels, two side panels, a top panel and a bottom panel. All panels are arranged and configured to connect or otherwise interact with adjacent panels in a fashion (e.g. permanently fixed, pivotally attached, overlapping, etc) that prevents or inhibits leakage of radiation from an interior of said enclosure during use as a radiation shield. According to one embodiment, the top panel may be pivotally attached to said back panel, and the front panel may be pivotally attached to one of the bottom or side panels. In any event, the rectangular box is dimensioned to receive within a radioactive fluid pump for the delivery of radioactive fluids to a patient. The back panel, two side panels, top panel and bottom panel are constructed of a material and thickness sufficient to shield medical personnel from radiation from radioactive materials contained within or passing through said fluid pump enclosure. According to a further embodiment, the fluid pump enclosure contains therewithin a radioactive fluid pump.

According to a further embodiment of the invention, there is provided an apparatus for shielding medical personnel from radioactive medical fluids being administered to a patient, comprising a medical syringe; a radioactive fluid pump, a fluid pump enclosure; and a syringe radiation shield; said fluid pump enclosure comprising a rectangular box comprising front and back panels, two side panels, a top panel and a bottom panel. All panels are arranged and configured to connect or otherwise interact with adjacent panels in a fashion (e.g. permanently fixed, pivotally attached, overlapping, etc) that prevents or inhibits leakage of radiation from an interior of said enclosure during use as a radiation shield. According to one embodiment, the top panel may be pivotally attached to said back panel, and the front panel may be pivotally attached to one of the bottom or side panels. In any event, the rectangular box is dimensioned to receive within a radioactive fluid pump for the delivery of radioactive fluids to a patient. The back panel, two side panels, top panel and bottom panel are constructed of a material and thickness sufficient to shield medical personnel from radiation from radioactive materials contained within or passing through said fluid pump enclosure The syringe radiation shield may comprise a first rod having a first proximal end and a second distal end and a first rod central bore extending between and through said first and second ends, said first rod central bore dimensioned to receive a fluid containing portion of said medical syringe; a second rod having a third end and a fourth end, and a second rod central bore extending partially but not entirely from said third end toward said fourth end, wherein said third end is configured to attach to said second end of said first rod in a threaded male-female connection, said second rod central bore dimensioned to receive a fluid lock at a forward end of said medical syringe; a third rod having a fifth end and a sixth end, and a third rod central bore extending partially but not entirely from said fifth end toward said sixth end, wherein said fifth end is configured to attach to said first end of said first rod in a threaded male-female connection, said third rod central bore dimensioned to receive a plunger portion of said medical syringe; wherein walls of said first, second, and third rods are made of a material and thickness sufficient to shield medical personal from radiation from radioactive materials contained in said syringe.

DETAILED DESCRIPTION

Figure 1:
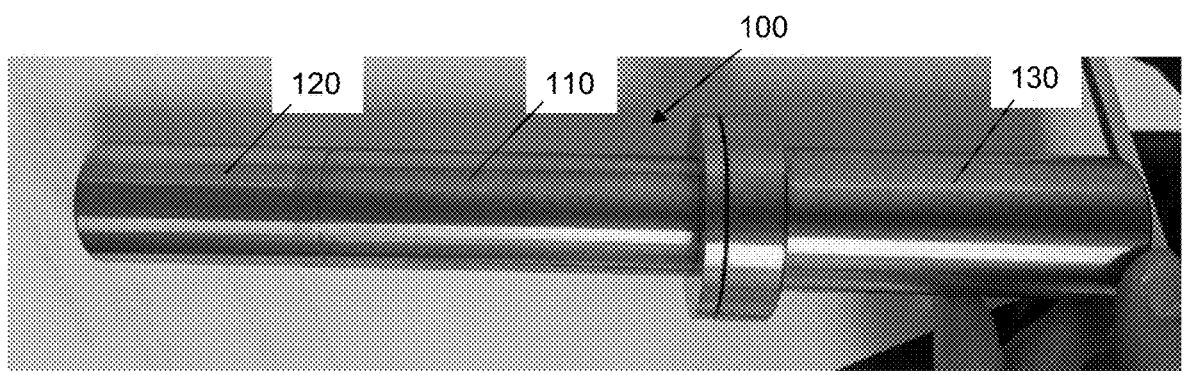
FIG. 1 is perspective view of a syringe carrier according to an embodiment of the invention.
Figure 2:
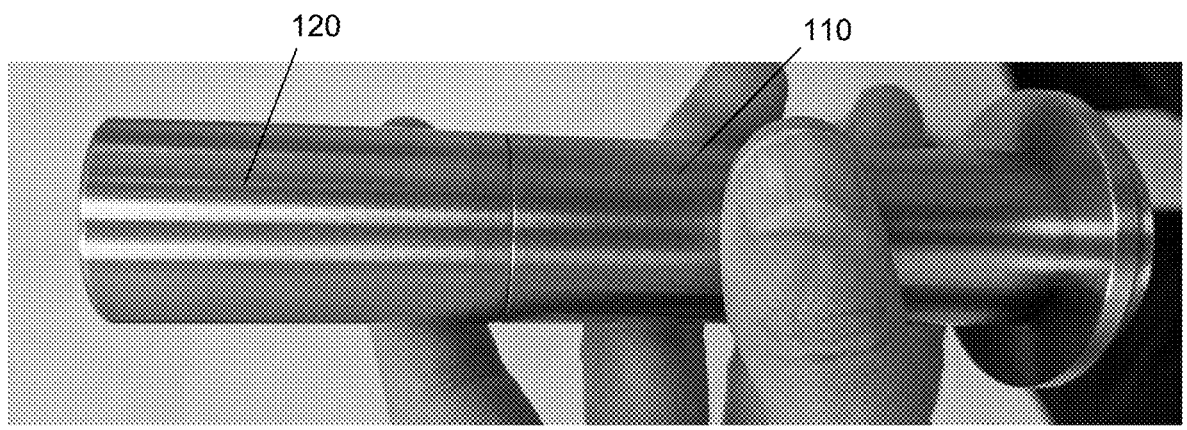
FIG. 2 is a perspective view of a syringe carrier main body and distal end cover according to an embodiment of the invention.
Figure 3:
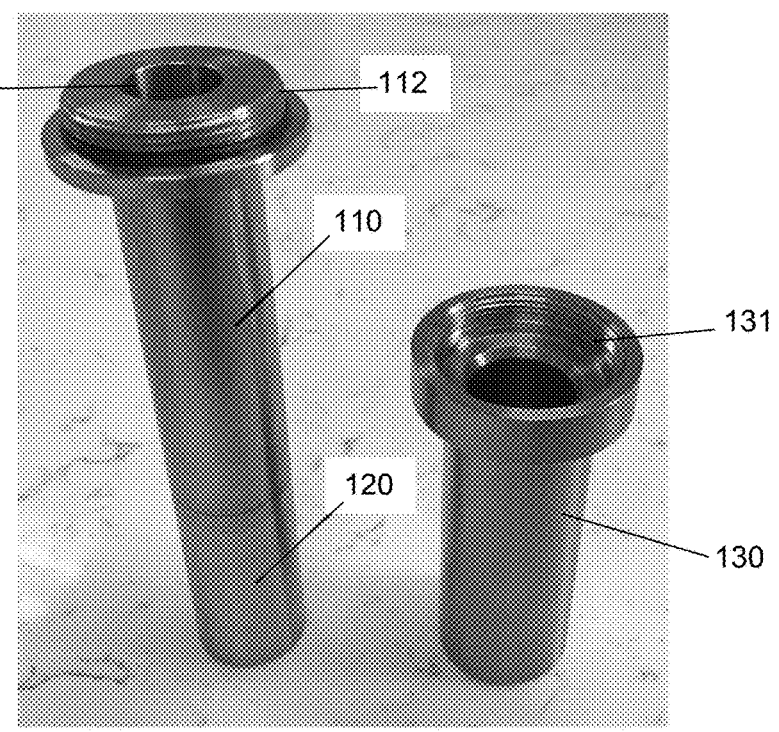
FIG. 3 is a side perspective view of a syringe carrier according to an embodiment of the invention.
Figure 4:
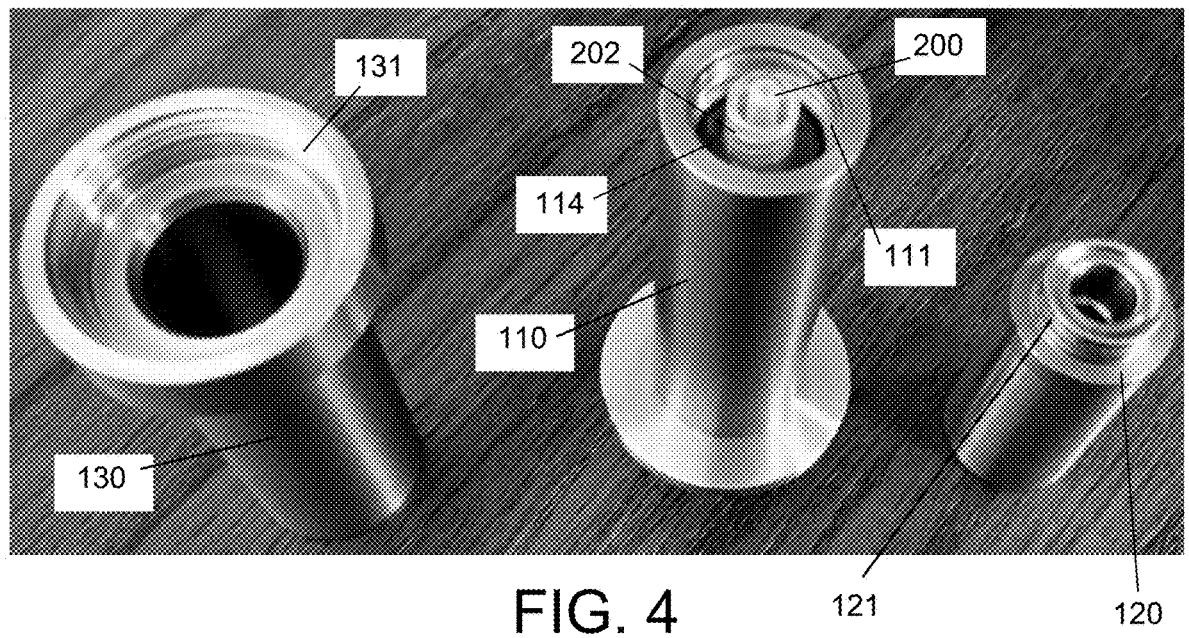
FIG. 4 is an overhead perspective view of a syringe carrier main body, distal end cover and proximal end cover according to an embodiment of the invention.
Figure 5:
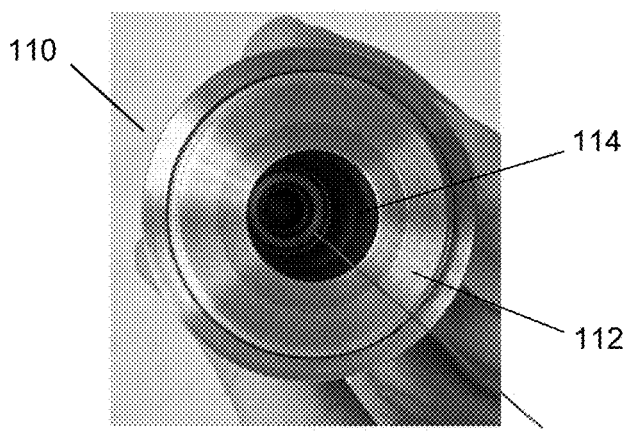
FIG. 5 is a closeup view of the proximal end of the syringe carrier main body according to an embodiment of the invention.

The invention may be understood by referring to the following description and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Unless otherwise indicated, all dimensions shown in the attached drawings are exemplary only and should not be construed as limiting the scope of the invention to those specific dimensions.

In accordance with certain aspects of an embodiment of the invention, a syringe shield is provided for receiving and transporting a syringe while shielding medical personnel from exposure to radiation emitted from a dosage within the syringe. The syringe shield is configured to remain with the syringe and continue at least partial shielding during injecting into a patient using a motorized pump. With particular reference to FIGS. 1-6, syringe shield 100 is provided and has main body syringe carrier 110, distal end cover 120, and proximal end cover 130. As best viewed in FIG. 4, distal end cover 120 includes an externally threaded coupling 121 that is configured for removable attachment to a threaded receiver 111 on main body syringe carrier 110. Similarly, proximal end cover 130 includes an internally threaded receiver 131 that is configured for removable attachment to an externally threaded coupling 112 (see, FIGS. 3 and 5) at the proximal end of main body syringe carrier 110. Main body syringe carrier 110, distal end cover 120, and proximal end cover 130 are thus configured for removable attachment to one another. Moreover, main body syringe carrier 110 includes an internal channel 114 extending there through from the proximal end to the distal end of main body syringe carrier 110, which internal channel 114 is sized and shaped to receive a syringe 200. More particularly, internal channel 114 is sized and shaped such that when syringe 200 is inserted fully within internal channel 114, the distal end of the syringe 200 extends outward from the distal end of main body syringe carrier, thus allowing access to the fluid lock 202 (such as a luer lock) of the syringe when distal end cover 120 is removed from syringe shield 100. Preferably, internal channel 114 may include a rim 116 that received a forward edge of the syringe 200 such that only the fluid lock 202 is exposed through the distal end of main body syringe carrier 110. Likewise, proximal end cover 130 has a hollow channel extending into its body such that a plunger of syringe 200 may be extended from the rest of syringe 200 even when the full syringe shield 100 has been assembled.

Figure 6:
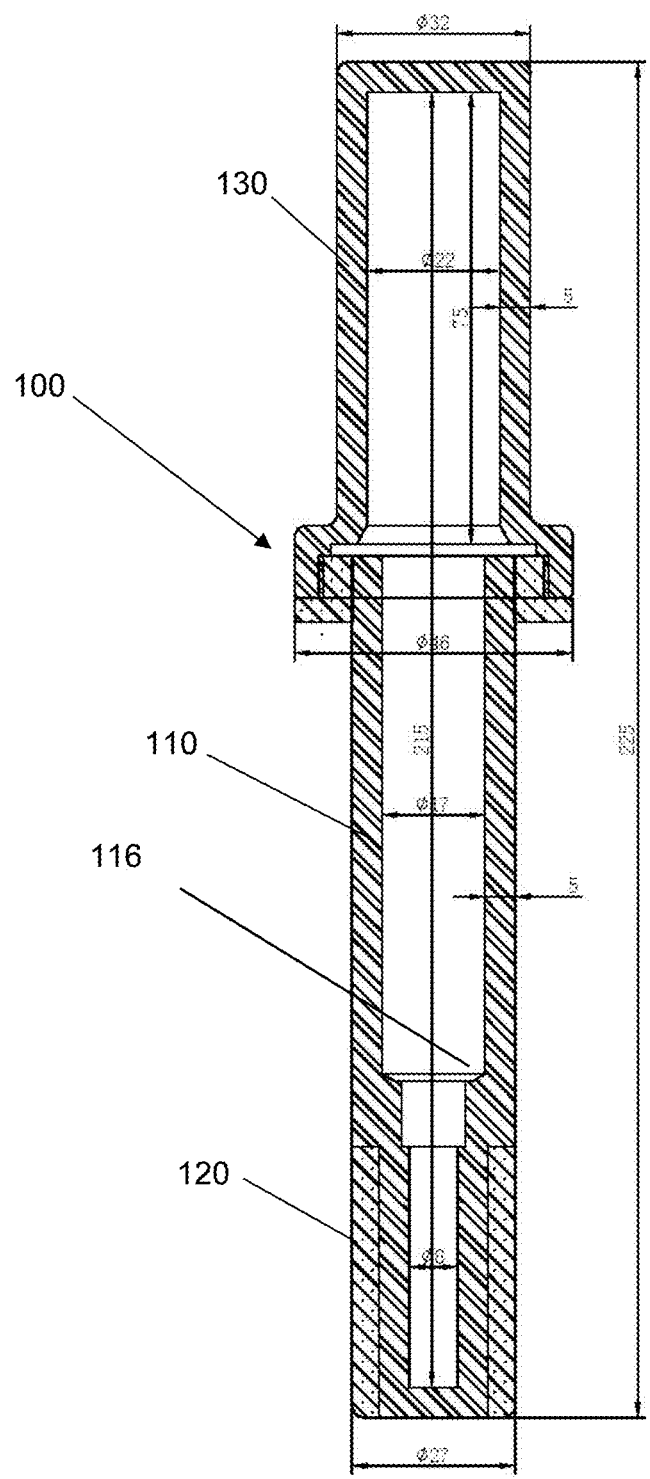
FIG. 6 is a cutaway view of an assembled syringe carrier according to an embodiment of the invention.
Figure 7:
FIG. 7 is a perspective view of a pump enclosure according to an embodiment of the invention.
Figure 8:
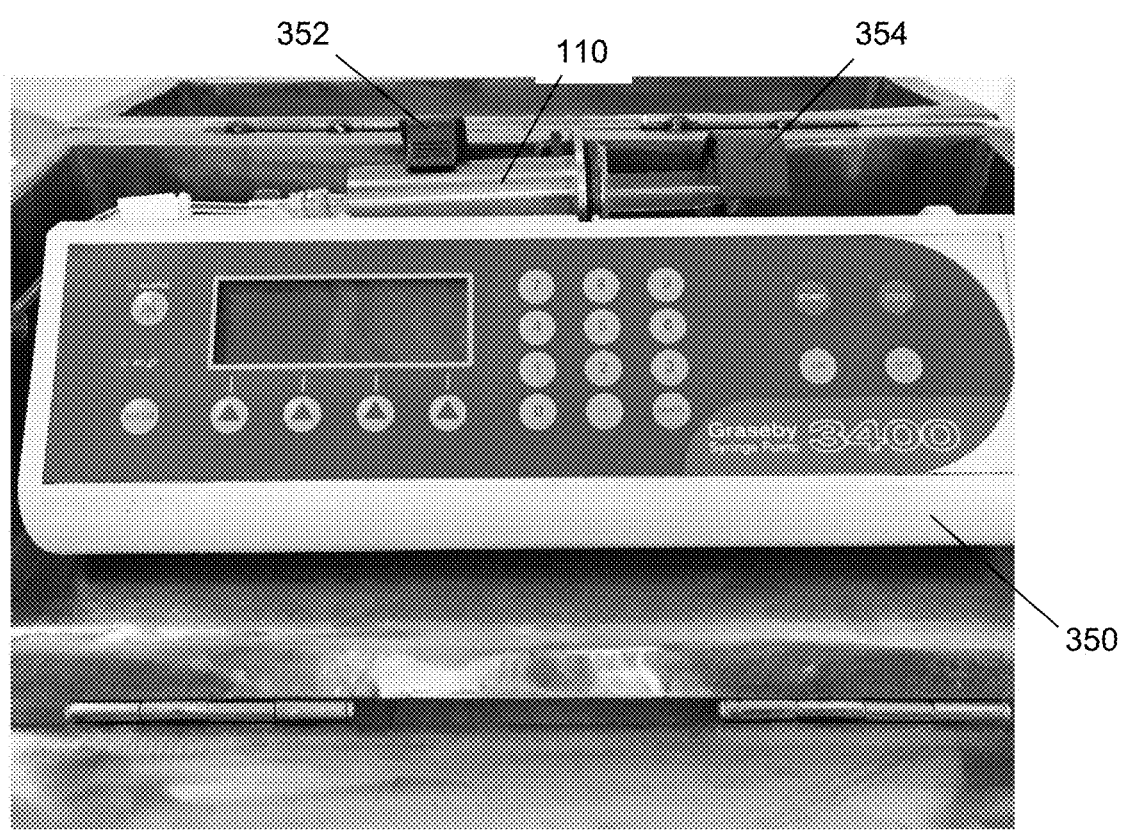
FIG. 8 is a close-up front view of a pump situated inside a pump enclosure with the lid and front panel in the open positions according to an embodiment of the invention.
Figure 9:
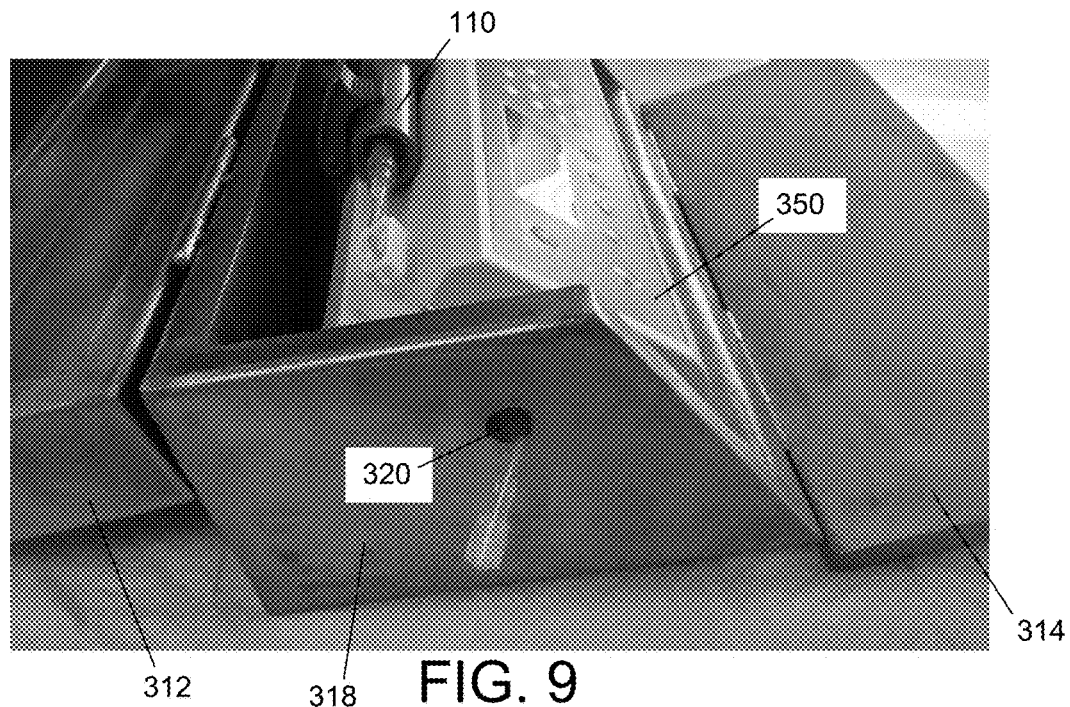
FIG. 9 is a side perspective view of a pump situated inside a pump enclosure with the lid and front panel in the open positions according to an embodiment of the invention.
Figure 10:
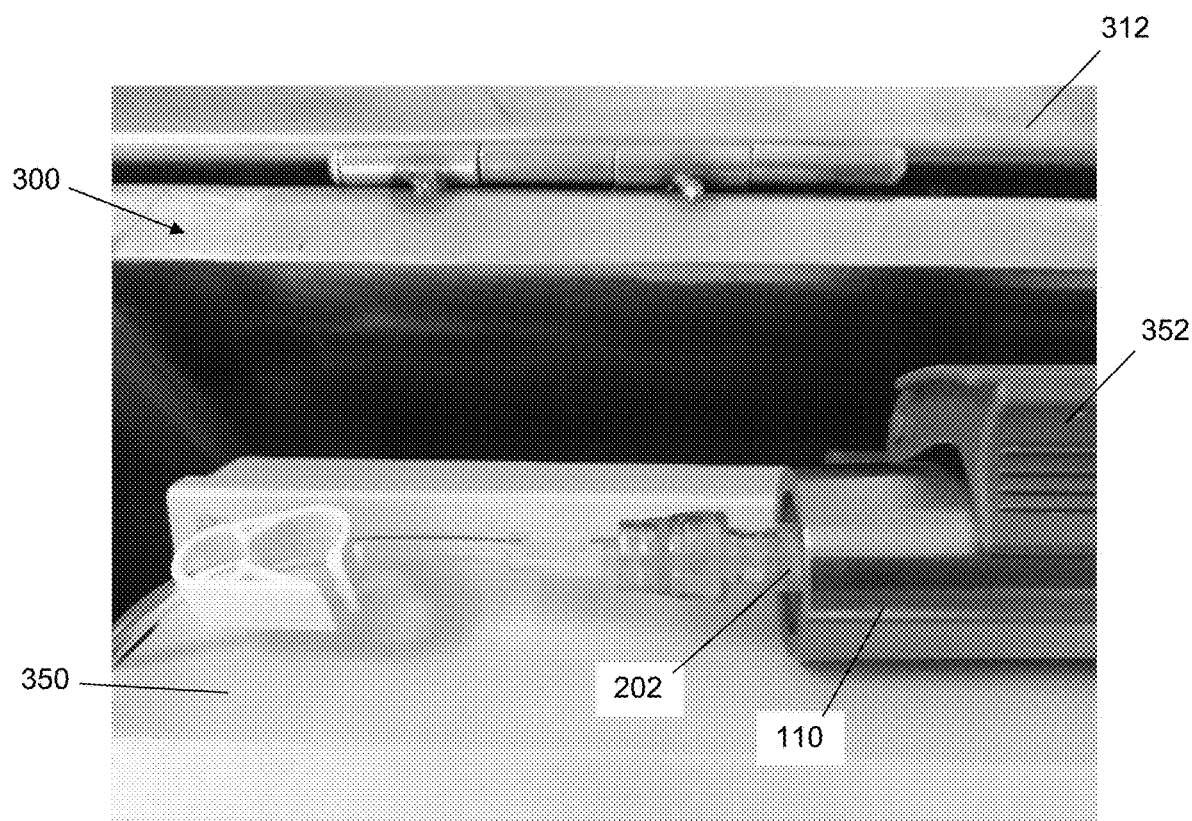
FIG. 10 is a closeup view of the top of a pump situated inside a pump enclosure with a syringe carrier main body held to the top of the pump via a clip.
Figure 11:
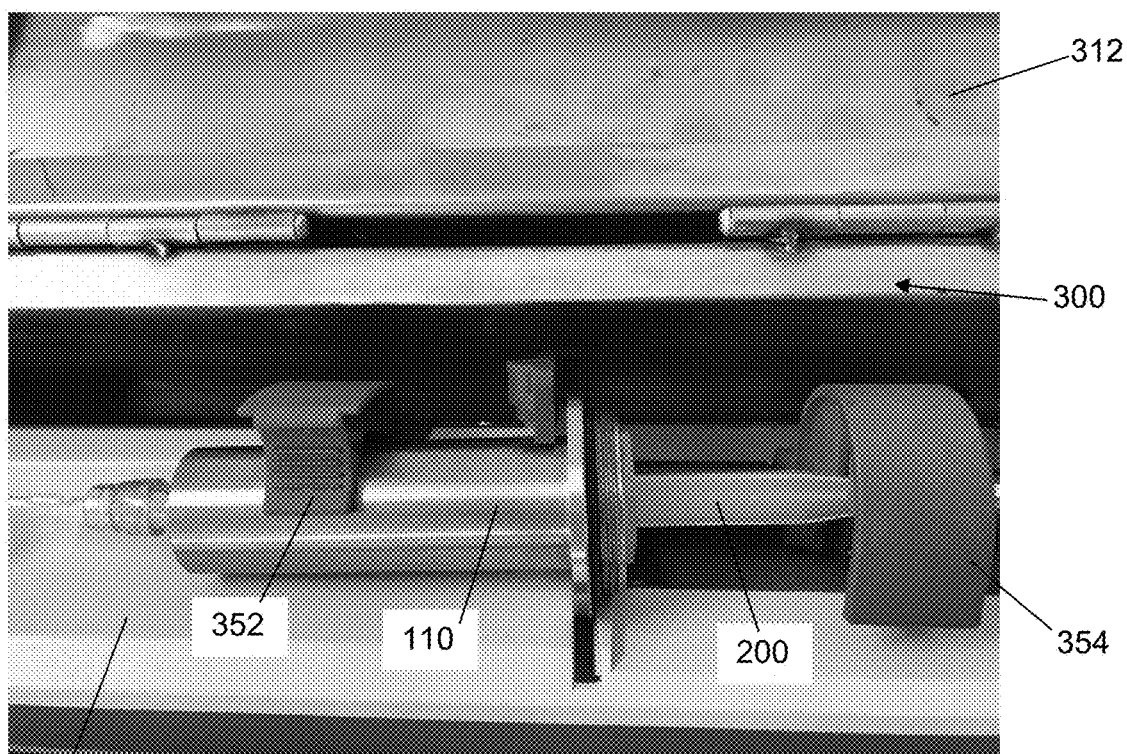
FIG. 11 is wider view of the embodiment shown in FIG. 10.
Figure 12:
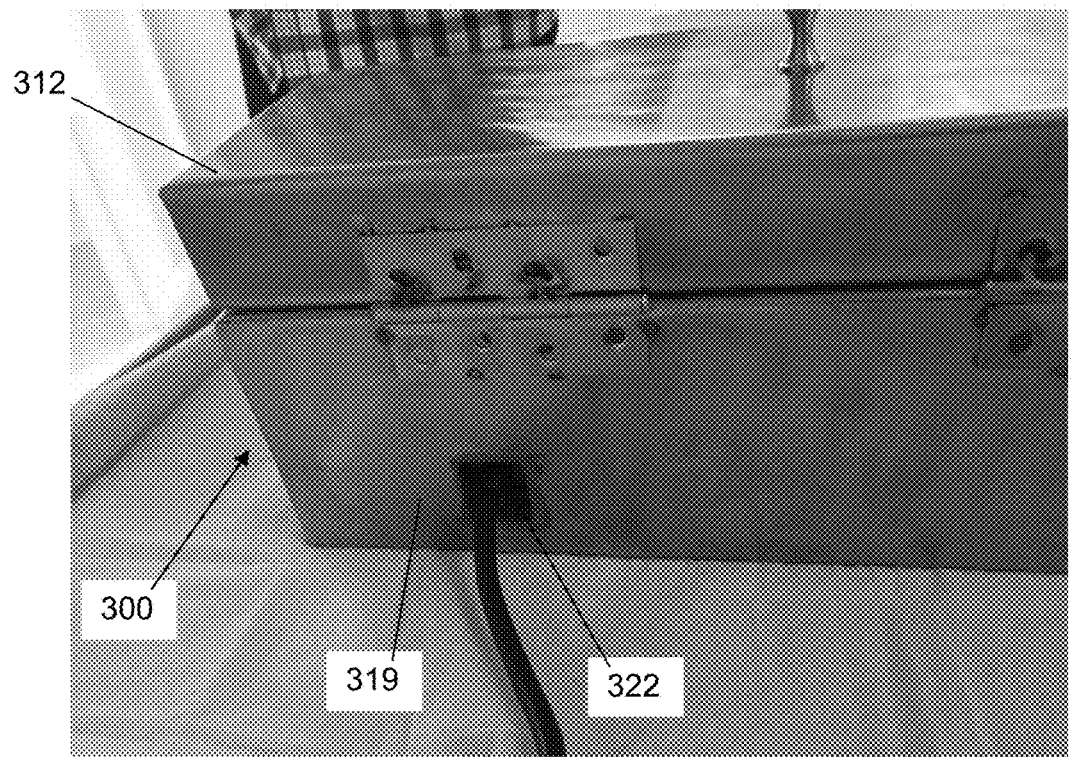
FIG. 12 is a partial rear perspective view of a pump enclosure according to an embodiment of the invention.

In accordance with certain aspects of an embodiment of the invention, FIG. 6 provides a cross-sectional view of syringe carrier 100 with exemplary dimensions shown for the above-described components. However, the thicknesses of the components of syringe carrier 100 may be varied depending upon the size of the pump that is to be used to administer the dosage, as discussed in greater detail below. By way of non-limiting example, each of main body syringe carrier 110, distal end cover 120, and proximal end cover 130 may have a wall thickness of 5 mm as shown in FIG. 6, but may alternatively have a wall thickness of up to 12 mm. Further, each of main body syringe carrier 110, distal end cover 120, and proximal end cover 130 is preferably formed of tungsten. It is of note that 11 mm of tungsten has been shown to block 90% of the radiation emitted from Zr-89, having approximately the same shielding effect as 32 mm of lead.

Next and with regard to further aspects of an embodiment of the invention, and with reference to FIGS. 7-12, a pump enclosure 300 is also provided, which pump enclosure 300 is configured to receive a pump 350 for dispensing a dosage from syringe 200 while syringe 200 is maintained within main body syringe carrier 110 of syringe shield 100. Pump enclosure 300 includes a lid 312, a front panel 314, a first side panel 316, a second side panel 318, a rear panel 319, and a bottom panel. Either one or both of lid 312 and front panel 314 may be separately and independently attached to pump enclosure 300 in a way that allows access to pump 350. More particularly, lid 312 may be opened to expose the top of pump 350 and (as explained in more detail below) syringe carrier 100 positioned on top of pump 350, with front panel 314 either opened or closed. Likewise, front panel 314 may be opened to expose the front control panel of pump 350, with lid 312 either opened or closed. Such independently openable panels 312 and 314 help to limit radiation exposure when an operator requires access to either of syringe carrier 100 or pump 350.

Each wall of pump enclosure 300 preferably includes lead encased in stainless steel, the dimensions of which may be adjusted by those skilled in the art to balance radiation shielding, overall weight, and dimensions for a particular pump as appropriate for given implementations. Pump enclosure 300 is formed so as to minimize gaps between movable portions, and thus to minimize gaps in the radiation shielding provided by the enclosure.

Pump 350 preferably includes a clip 352 preferably attached at or near a top surface of the pump and configured to removably hold main body syringe carrier 110 of syringe shield in place during injection of the dosage from syringe 200. Clip 352 preferably wraps around main body of syringe carrier 110 (when placed in the dispensing position on top of pump 350), and thus holds syringe carrier 110 in place as pump drive 354 pushes the plunger of syringe into the body of syringe 200 to dispense the dose. Pump 350 is preferably programmable such that the dispensing operation may be automatically carried out after an operator has placed main body syringe carrier 110 on pump 350 and programmed the dosage settings in pump 350, thus allowing the entire assembly of pump 350, syringe 200, and main body syringe carrier 110 to be maintained within shielded pump enclosure 300 throughout the dosing operation.

Side panel 318 may include a discharge outlet 320 through which a fluid line may extend from syringe 200 within main body syringe carrier 110 to outside of pump enclosure 300, and ultimately to supply the dosage to an intravenous line extending to the patient. Further, rear panel 319 may have a power port that may allow passage of a power cable from pump 300 to a power supply outside of enclosure 300. Alternatively, pump 300 may be battery operated so as to avoid the need for extending a power cable outside of enclosure 300, and thus providing further radiation shielding.

In use, after preparation of a dosage of a radioactive agent, and more particularly Zr-89, that is to be injected into a patient and its placement inside of a syringe 200, and in accordance with still further aspects of the invention, syringe 200 may be placed inside of main body syringe carrier 110 of syringe shield 100. Thereafter, distal end cover 120 may be threaded onto the distal end of main body syringe carrier 110, and proximal end cover 130 may be threaded onto the proximal end of main body syringe carrier 110. With that dosage of Zr-89 then contained within syringe shield 100, the dosage may be transported from its place of preparation to the patient. There, an operator may remove distal end cover 120 and proximal end cover 130 from main body syringe carrier 110, and place main body syringe carrier 110 (with syringe 200 therein) on top of pump 350 positioned within pump enclosure 300. After the fluid connection is made between syringe 200 and the fluid line extending to discharge outlet 320, the plunger of syringe 200 may be placed in contact with pump drive 354, clip 352 may be placed over main body syringe carrier 110 to hold it in place, and lid 312 may be closed to further shield medical personnel and the patient from radiation emitted from the dosage in syringe 200. The operator may then use the control panel on the front of pump 350 to modify and/or finalize any dosage settings and initiate the injection process, and thereafter close front panel 314 so as to fully encase syringe 200, main body syringe carrier 110, and pump 350 within the protective shielding of pump enclosure 300 for the duration of the injection process.

While not shown in the Figures, optionally one or more observation windows may be provided in lid 312 and/or front panel 314 of pump enclosure 300 to allow an operator to observe the pump operation and the dispensing operation.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

The invention claimed is:
1. A syringe radiation shield consisting essentially of:
a first rod having a first end and a second end and a first rod central bore extending between and through said first and second ends, said first rod central bore dimensioned to receive a fluid containing portion of a medical syringe;
a second rod having a third end and a fourth end, and a second rod central bore extending partially but not entirely from said third end toward said fourth end, wherein said third end is configured to attach to said second end of said first rod in a threaded male-female connection, said second rod central bore dimensioned to receive a fluid lock at a forward end of said medical syringe;
a third rod having a fifth end and a sixth end, and a third rod central bore extending partially but not entirely from said fifth end toward said sixth end, wherein said fifth end is configured to attach to said first end of said first rod in a threaded male-female connection, said third rod central bore dimensioned to receive a plunger portion of said medical syringe;
wherein walls of said first, second, and third rods are made of a material and thickness sufficient to shield medical personal from radiation from radioactive materials contained in said medical syringe.

2. A fluid pump enclosure comprising:
a rectangular box comprising front and back panels, two side panels, a top panel and a bottom panel,
said top panel arranged and configured to permit user access to contents of said rectangular box,
said front panel arranged and configured to permit user access to said contents,
said rectangular box dimensioned to receive within a radioactive fluid pump for the delivery of radioactive fluids to a patient;
each of said front panel, said back panel, said two side panels, said top panel and said bottom panel constructed of a material and thickness sufficient to shield medical personnel from radiation from radioactive materials contained within or passing through said fluid pump enclosure.

3. The fluid pump enclosure according to claim 2, further comprising said radioactive fluid pump.

4. An apparatus for shielding medical personnel from radioactive medical fluids being administered to a patient, comprising
a medical syringe;
a radioactive fluid pump,
a fluid pump enclosure; and
a syringe radiation shield;
said fluid pump enclosure comprising
a rectangular box comprising front and back panels, two side panels, a top panel and a bottom panel,
said top panel arranged and configured to allow user access to a top of said radioactive fluid pump,
said front panel arranged and configured to allow user access to a front of said radioactive fluid pump,
said rectangular box dimensioned to receive said radioactive fluid pump;
each of said front panel, said back panel, said two side panels, said top panel and said bottom panel constructed of a material and thickness sufficient to shield medical personnel from radiation from radioactive materials contained within or passing through said fluid pump enclosure;
said syringe radiation shield comprising,
a first rod having a first end and a second end and a first rod central bore extending between and through said first and second ends, said first rod central bore dimensioned to receive a fluid containing portion of said medical syringe;
a second rod having a third end and a fourth end, and a second rod central bore extending partially but not entirely from said third end toward said fourth end, wherein said third end is configured to attach to said second end of said first rod in a threaded male-female connection, said second rod central bore dimensioned to receive a fluid lock at a forward end of said medical syringe;
a third rod having a fifth end and a sixth end, and a third rod central bore extending partially but not entirely from said fifth end toward said sixth end, wherein said fifth end is configured to attach to said first end of said first rod in a threaded male-female connection, said third rod central bore dimensioned to receive a plunger portion of said medical syringe;
wherein walls of said first, second, and third rods are made of a material and thickness sufficient to shield medical personal from radiation from radioactive materials contained in said medical syringe.

5. The apparatus according to claim 4, further comprising a radioactive medical fluid contained in said medical syringe.

* * * * *